United States Patent
Yanagawa

[11] Patent Number: 5,530,003
[45] Date of Patent: Jun. 25, 1996

[54] PHARMACEUTICAL COMPOSITIONS FOR CURING RHEUMATISM

[75] Inventor: Akira Yanagawa, Yokohama, Japan

[73] Assignee: Dott Limited Company, Japan

[21] Appl. No.: 170,220

[22] PCT Filed: Apr. 30, 1993

[86] PCT No.: PCT/JP93/00587

§ 371 Date: Dec. 28, 1993

§ 102(e) Date: Dec. 28, 1993

[87] PCT Pub. No.: WO93/21922

PCT Pub. Date: Nov. 11, 1993

[30] Foreign Application Priority Data

May 1, 1992 [JP] Japan ..................... 4-139705

[51] Int. Cl.⁶ .................... A01N 43/54

[52] U.S. Cl. .............. 514/256; 514/274; 252/182.12

[58] Field of Search .................... 514/256, 274

[56] References Cited

PUBLICATIONS

J. Sur. Res, 14[3] (1973) pp. 247–253.
Ann. Rheum Dis, 46 [10], (1987 Oct.) pp. 763–767.

Primary Examiner—Paul J. Killos
Attorney, Agent, or Firm—Lorusso & Loud

[57] ABSTRACT

Disclosed is a novel agent for curing rheumatism, which consists of a pharmaceutical composition containing 5-fluorouracil or an N-derivative thereof to be converted into 5-fluorouracil within the body, which is less in side effects, which has a high degree of safety, and which is high in curing effects.

6 Claims, No Drawings

PHARMACEUTICAL COMPOSITIONS FOR CURING RHEUMATISM

DESCRIPTION

This application is a 371 of PCT/JP93/00587 filed Apr. 30, 1993.

TECHNICAL FIELD

The present invention relates to a novel pharmaceutical composition for curing rheumatism.

BACKGROUND ART

Chronic articular rheumatism is a chronic systemic inflammatory disease involved mainly with the joints and patients with rheumatism suffer from the difficulties in daily life due to disorders of the functions of the joints.

Salicylic acid has been employed as medicine for curing rheumatism for a long time. Currently, there have extensively been employed sodium gold thiomalate, penicillamine, auranofin, lobenzarit 2Na, bucillamin, methotrexate (MTX), and so on. These medicine, however, cannot be said satisfactory, fox example, because they are low in the curing effects, short in pharmaceutical continuity, and they have some severe side effects.

DISCLOSURE OF INVENTION

The present invention has the object to provide a novel pharmaceutical composition for curing rheumatism having low in side effects, high in safety and superior in curing effects.

As a result of extensive research with the attempt to solve the problems inherent in such conventional compositions as described hereinabove, it has been found that 5-fluorouracil, employed currently as an anti-tumor agent, or an N-derivative thereof to be converted into 5-fluorouracil within the body, can exhibit a high degree of pharmaceutical activity as an agent for curing rheumatism. This invention has been completed on the basis of this finding.

The present invention provides a pharmaceutical composition for curing rheumatism containing, as an active ingredient, 5-fluorouracil or an N-derivative thereof to be converted into the 5-fluorouracil within the body.

The 5-fluorouracil (5-FU) to be employed as the active ingredient according to the present invention may be represented by the following general formula:

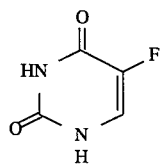
(1)

Further, the substance to be converted into the 5-fluorouracil within the body is an N-derivative of the 5-fluorouracil and there may be mentioned tegafur and doxyfurlysine as will be described hereinafter:

Tegafur (2)

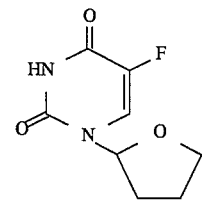

Doxyfurlysine (3)

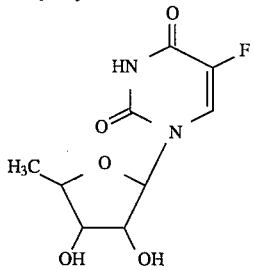

The 5-fluorouracil and the N-derivative thereof may be employed together with a modulator which may be employed when the 5-fluorouracil or its N-derivative is employed as an anti-tumor agent. Although, for example, methotrexate and leucovolin may be employed as a modulator, there may preferably be employed uracil as represented by the general formula:

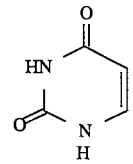
(4)

The rate of the uracil to be formulated may be approximately 4 moles per mole of the 5-fluorouracil or the N-derivative thereof.

The pharmaceutical composition for curing rheumatism according to the present invention may be administered in conventional manner, such as via an oral route or by injection. The daily dosage of the agent may range from 300 mg to 1,200 mg and it is preferred to administer the daily dosage three or four times.

The pharmaceutical composition for curing rheumatism according to the present invention is of a type novel and different from conventional ones and it can demonstrate the high extent of efficacy and long pharmaceutical continuity against chronic articular rheumatism, without showing any severe side effects.

BEST MODE FOR CARRYING OUT THE INVENTION

EXAMPLES

The present invention will be described more in detail by way of examples.

EXAMPLE 1

The following experiment was carried out by using a pharmaceutical agent (agent A) with tegafur and uracil formulated in the mole ratio of 1 to 4 (tegafur: uracil) and with only tegafur (agent B).

The agents A and B were tested for their ability of migration into the tissues on an adjuvant arthritis model.

Eight-week SD-type male rats (JCL) were subcutaneously injected in the paws of their right rear legs with a suspension of Mycobacterium butyricum in liquid paraffin (0.6 mg/0.1 ml; Difco). The rats with arthritis occurred in the 15th day were selected as test animals and each group consisting of eight rats was subjected to the test.

The test animals were orally administered with a solution or suspension of the agent A (tegafur, 15 mg/kg; uracil, 33.6 mg/k) or the agent B (tegafur, 15 mg/kg) in a 5% gum arabi solution. In four hours after the oral administration, the extent of migration of each of the agents A and B into the tissues (plasma, the foot inoculated with Mycobacterium butyricum, and the foot non-inoculated therewith) was measured by conventional method.

The test results revealed that each of the agents A and B showed a high degree of migration into the tissues. Further, no big difference in the concentration of tegafur in the tissues was recognized between the group in which the agent A was administered and the group in which the agent B was administered; however, there was recognized a big difference in the concentration of 5-fluorouracil in the tissues between the two groups and it was found that the group in which the agent A was administered was higher in the concentration of 5-fluorouracil in the tissues than the group in which the agent B was administered. This is considered to indicate the possibility that the combination of tegafur with uracil has suppressed the metabolism of 5-FU as the active compound at the site of inflammation close to rheumatism.

EXAMPLE 2

This example shows a case in which patients with rheumatism were treated with the agent A.

(i) Patients treated

Treated patients presented with chronic articular rheumatism (RA) according to American Rheumatism Association (ARA, revision in 1987) were determined having the moderate activity or higher according to the ARA's standard for determining activities of rheumatism at the time of initiating the administration of the agent A. Further, it should be noted that the patients were the one who could not be administered with any commercially available remission introducing agent such as a gold salt, D-penicillamine and so on due to non-reaction or side effects and who rejected the administration of an adreno-cortical hormone. It was noted herein that, in carrying out the test, the purposes of the test, the contents of the test, the duration, expected clinical effects, predicted side effects, and so on were explained well to the patients, and the consent of participation in the test was obtained from the patients.

(ii) Test method

The duration of the administration of the agent A was determined as six weeks or shorter. The dose of the agent A was one capsule (containing 100 mg of tegafur and 224 mg of uracil) and one capsule was administered three times daily after each meal.

During the administration of the agent A, the use of a non-steroid anti-inflammatory agent was not changed and no additional injection of any immunosuppressive agent, immunomodulator and adrenocortical hormone agent into the joints was made.

Clinical evaluation was made according to Lansbury's activity index (calculated from the sum of continual period of stiffness, the grasping power, the erythrocyte sedimentation rate (E.S.R), the number of joints (the number of joints causing a pain)). The number of joints was counted according to the method of McCarty et al. (J. L. Hollander and D.J. McCarty: Arthritis And Allied Condition, 8th Edition, Lea & Febiger, Philadelphia; p. 419, 1974).

In addition, clinical investigations were also carried out about parameters for various kinds of inflammation to be employed for usual RA efficacy tests, immunoglobulins (IgG, IgA and IgM), serum, biochemistry, and so on. Subjective impression of the patients for the agent A was determined by themselves by five ratings (much better than before, better than before, not improved yet worse, worse than before, and much worse than before), compared with the state prior to the initiation of the administration of the agent A.

The occurrence of side effects and accompanying symptoms was determined with respect to the causal relationship with the agent A by five ratings (absent, probably absent, absent or present, probably present, and present).

Comprehensive evaluation was carried out at the time of the completion of the test by the extent of final and total improvements, overall safety and utility. The extent of the final and total improvements was evaluated on the efficacy evaluation items upon administration of the agent A by seven ratings (remarkably improved, improved, slightly improved, nothing changed, slightly worsened, worsened, and considerably worsened), compared with efficacy evaluation items made at the time of initiating the administration of the agent A.

The extent of the overall safety was evaluated on the basis of the side effects and clinical test results obtained by the administration of the agent A by four ratings (safe, roughly safe, questionable, and not safe).

The extent of the utility was totally evaluated on the basis of the extent of the final and total improvements and the extent of the overall safety by seven ratings (extremely useful, useful, slightly useful, useful or non-useful, slightly undesirable, undesirable, and extremely undesirable).

(iii) Curing results

Six patients were treated with the agent A and the clinical results obtained in 12 weeks after administration are shown in Tables 1 and 2 below. Table 1 indicates the transition of various parameters before and after the administration of the agent A and Table 2 indicates the transition of each evaluation item before and after the administration of the agent A.

TABLE 1

| ITEMS | | BEFORE → AFTER |
|---|---|---|
| E.S.R. | MEAN | 70.4 → 35 |
| (mm/hour) | S.D. | 29.7 → 19.7 |
| STIFFNESS | MEAN | 91 → 7 |
| IN THE MORNING | S.D. | 152.2 → 8.4 |
| (minutes) | | |
| GRASPING POWER | MEAN | 120 → 154.2 |
| (mmHg) | S.D. | 86.9 → 86.2 |
| NO. OF JOINTS | MEANS | 86.6 → 30.4 |
| | S.D. | 20.2 → 24.9 |
| LANSBURY | MEAN | 63.2 → 29.4 |
| INDEX (%) | S.D. | 30.3 → 13.7 |

TABLE 2

| ITEMS | | BEFORE → AFTER (FLUCTUATION RATE) |
|---|---|---|
| LANSBURY | MEAN | 63.2 → 29.4 (53.5%) |
| INDEX | S.D. | 30.3 → 13.7 |
| CRP | MEAN | 13.1 → 4.0 (69.5%) |

TABLE 2-continued

| ITEMS | | BEFORE → AFTER (FLUCTUATION RATE) |
|---|---|---|
| (mg/dl) | S.D. | 10.2 → 2.2 |
| RAHA | MEAN | 1024 → 112 (89.1%) |
| (times) | S.D. | 944 → 44 |
| IgG | MEAN | 1713 → 1406 (17.9%) |
| (mg/dl) | S.D. | 331 → 300 |
| IgA | MEAN | 268.2 → 227.0 (15.4%) |
| (mg/dl) | S.D. | 48.0 → 51.5 |
| Igm | MEAN | 194.2 → 133.2 (31.4%) |
| (mg/dl) | S.D. | 64.1 → 57.4 |

The Lansbury's activity index, as computed from the continuous time of stiffness in the morning, as represented in minutes, the grasping power, as represented in mmHg, the E.S.R., as represented in mm per hour, and the activity function, was found to decrease from 63.2% ±30.3% before administration to 29.4%±13.7% after administration at the fluctuation rate of 53.5%. The fluctuation of the individual parameters has indicated improvements in the number of the joints from 86.6±20.2 before administration to 30.4±24.9 (p=0.004) after administration, in the grasping power from mmHg±86.9 mmHg before administration to 154.2 mmHg ±86.2 mmHg after administration, in the E.S.R. from 70.4 mm/hour±29.7 mm/hour before administration to 35 mm/hour ±19.7 mm/hour (p=0.057) after administration, and in the extent of stiffness in the morning from 11.5±15.26 minutes before administration to 7±8.4 minutes after administration.

The CRP has decreased from 13.1 mg/dl±10.2 mg/dl before administration to 4.0 mg/dl±2.2 mg/dl after administration at the fluctuation rate of 69.5%.

The RAHA has improved from a mean value of 1024 times±944 times at the time of initiating the administration of the agent A to a mean value of 112 times ±44 times after administration at the fluctuation rate of 89.1%.

The transition of the various immunoglobins (IgG, IgA and IgM) indicates that IgG fluctuates from 1713 mg/dl±331 mg/dl to 1406 mg/dl±300 mg/dl at the fluctuation rate of 17.9%; IgA fluctuates from 268.2 mg/dl ±48.0 mg/dl to 227.0 mg/dl ±51.5 mg/dl at the fluctuation rate of 15.4%; and IgM fluctuates from 194.2 mg/dl±64.1 mg/dl to 133.2 mg/dl±57.4 mg/dl at the fluctuation rate of 31.4%

When the fluctuation of the RAHA is compared with the fluctuation of the immunoglobulins, it is found that the decrease in the RAHA is recognized alternately with the decrease in the IgM. Hence, it can be considered that the administration of the agent A has caused a decrease in IgM-RF although this test did not measure RF for each class.

Further, it is found from the extent of the final and total improvements that the administration of the agent A indicates the extent higher than improvements in four cases out of six cases (66.7%) and the extent higher than slight improvements in six cases out of six cases (100%).

The extent of the overall safety indicates the safety category in five cases out of six cases (83.3%), and an increase in eosilophils at the maximal rate of 14.8% was recognized in only one case (16.7%).

In the extent of the utility, it is found that five cases out of six cases (83.4%) is classified into a category higher than useful. Hence, the agent A was found to belong to a category of comparably strong anti-rheumatism agents.

From the above clinical results, the agent A can be determined as achieving the remarkably high degree of the curing effects for rheumatism at the daily dosage as low as 300 mg at three times.

More specifically, the curing effects achieved by the clinical examination over the short period of 16 weeks has shown improvements in the extent of stiffness in the morning, the pain, dolor and swelling of joints, the swelling of joints, comprehensive evaluation by the patients and medical doctors, test results, erythrocyte sedimentation rate, CRP, RAHA coagulation value, immunoglobulins (in particular IgM). A 50% or higher improvement in the Lansbury index was recognized in eight to ten weeks after the administration of the agent A. Hence, the pharmaceutical composition according to the present invention shows a comparably strong anti-rheumatism action.

Further, the pharmaceutical effects of the composition according to the present invention can be determined as comparable as MTX as an anti-rheumatism agent whose efficacy is said to occur in approximately three to eight weeks after the administration.

Although the side reaction, that is, increasing the eosinophils, was recognized in one case only, during the administration of the agent A, there was no case at all in which the administration should be suspended due to severe side effects.

I claim:

1. A pharmaceutical composition for alleviating the symptoms of rheumatism comprising (1) an active ingredient selected from the group 5-fluorouracil and N-derivatives of 5-fluorouracil which are converted into 5-fluorouracil within the body and (2) uracil.

2. A pharmaceutical composition as claimed in claim 1 wherein said active ingredient is tegafur.

3. A method for alleviating the symptoms of rheumatism in a patient comprising administering to said patient a pharmaceutical composition comprising (1) an active ingredient selected from the group consisting of 5-fluorouracil and N-derivatives of 5-fluorouracil which are converted into 5-fluorouracil within the body and (2) uracil.

4. The method of claim 3 wherein said active ingredient is tegafur.

5. The method of claim 3 wherein said administering is by an oral daily dosage of 300 mg to 1200 mg of said composition.

6. The method of claim 3 wherein said administering is by injection.

* * * * *